United States Patent [19]

Laine et al.

[11] Patent Number: 4,979,093
[45] Date of Patent: Dec. 18, 1990

[54] XYZ POSITIONER

[75] Inventors: Donald D. Laine, San Carlos; Jerry E. Rochte; Frederick C. Wolcott, both of Los Altos, all of Calif.

[73] Assignee: Cavro Scientific Instruments, Sunnyvale, Calif.

[21] Appl. No.: 361,713

[22] Filed: May 26, 1989

Related U.S. Application Data

[63] Continuation of Ser. No. 74,531, Jul. 16, 1987, abandoned.

[51] Int. Cl.$^5$ .......................... G05B 19/42; G05D 3/12
[52] U.S. Cl. .............................. 364/167.01; 364/513; 901/14
[58] Field of Search ............... 364/167.01, 513, 560, 364/520, 174, 474.37; 901/3, 9, 14, 22, 27, 37; 33/1 M; 414/736, 739; 156/645

[56] References Cited

U.S. PATENT DOCUMENTS

| | | | |
|---|---|---|---|
| 2,404,243 | 7/1946 | Moynihan | 89/41 |
| 2,847,859 | 8/1958 | Lynott | 74/37 |
| 3,473,751 | 10/1969 | Quenot | 242/67.2 |
| 3,529,481 | 9/1970 | Budzyn | 33/1 |
| 3,553,842 | 1/1971 | Gerber | 33/137 |
| 3,564,533 | 2/1971 | Linn | 33/1 |
| 3,665,608 | 5/1972 | Stockebrand | 33/1 M |
| 4,393,728 | 7/1983 | Larson et al. | 901/27 |
| 4,412,383 | 11/1983 | Landa | 33/1 M |
| 4,437,151 | 3/1984 | Hurt et al. | 364/560 |
| 4,484,293 | 11/1984 | Minucciani et al. | 364/560 |
| 4,485,453 | 11/1984 | Taylor | 364/560 |
| 4,500,749 | 2/1985 | Khoshnevis | 178/18 |
| 4,516,476 | 5/1985 | Beaton | 901/50 |
| 4,585,519 | 4/1986 | Jaffe et al. | 156/645 |
| 4,653,011 | 3/1987 | Iwano | 364/513 |
| 4,680,519 | 7/1987 | Chand et al. | 364/513 |
| 4,694,230 | 9/1987 | Slocum et al. | 364/513 |
| 4,698,775 | 10/1987 | Koch et al. | 364/513 |
| 4,813,146 | 3/1989 | Jaluzot | 33/1 M |

Primary Examiner—Jerry Smith
Assistant Examiner—Paul Gordon
Attorney, Agent, or Firm—Flehr, Hohbach, Test, Albritton & Herbert

[57] ABSTRACT

An XYZ positioner is disclosed. The XYZ positioner provides for positioning an XY or an XYZ orientation and has a wide range of applications, such as in the medical field, for dispensing various types of fluids, as desired.

23 Claims, 7 Drawing Sheets

XYZ POSITIONER

This is a continuation of application Ser. No. 074,531, filed July 16, 1987, now abandoned.

BACKGROUND OF THE INVENTION

The present invention relates to an XY or XYZ positioner for use in a wide range of positioning applications, including fluid handling in the medical field.

A problem with most prior art XYZ mechanisms is that such mechanisms require either heavy rectilinear mechanisms and associated support structures or heavy variable arm length structures. Weight and bulk of the Z axis mechanism is often located at the end of a cantilevered arm, and its weight and bulk get multiplied back through the rest of the system because the other two axes of motion have to support the heavy Z axis mechanism. It would be desirable to reduce the weight of the Z axis mechanism so that the weight, size and complexity of the whole system can be reduced.

Also, most prior art XYZ systems are complete systems that can not be easily tailored and changed for systems of varying geometries. It would be desirable to be able to build an XYZ system out of components which mount individually and separately. Such a system can produce different geometries simply by altering the mounting distance between the components.

Further, in prior art XYZ systems, either the area around the target area is encumbered with mechanism, or a large area in back of the target area is encumbered with mechanism. It would be desirable to put all of the mechanism on one side of the four-sided XY perimeter and to have that mechanism take up only a relatively small space.

SUMMARY OF THE INVENTION

It is an object of the present invention to provide an improved XYZ positioner.

The XYZ positioner includes two variable length arms and one fixed length arm, input means to accept information on how long the arm should be or should be changed, and means to change the length of the variable length arms. The arms are connected to form pivots such that the pivots at the end of the stationary arms are stationary.

The pivot which connects the two movable arms contains a probe head within the pivot structure. The unused length of arms are stored in a compact manner, such as on a reel. The stiffness of the unfurled arms is obtained by increasing the section modulus of the arms as they are unfurled. Means are provided to securely hold the unfurled arms at the pivot so that arm motion is constrained in a direction perpendicular to rotation.

The XYZ positioner can be placed in any type of orientation, as desired. The "XYZ" designation is for purposes of simplifying the description.

Further objects, features and advantages of the present invention will become apparent from the following detailed description when taken in conjunction with the accompanying drawings.

DETAILED DESCRIPTION OF THE DRAWINGS

As described above, the present invention relates to an XY or an XYZ positioner. It should be noted for purposes of explanation that the XYZ positioner can be placed in any type of orientation, as desired. The "XY" or "XYZ" designation is for purposes of simplifying the description.

By way of general overview, the XYZ positioner includes two variable length arms and one fixed length arm, input means to accept information on how long the arm should be or should be changed, and means to change the length of the variable length arms. The arms are connected to form pivots such that the pivots at the end of the stationary arms are stationary.

The pivot which connects the two movable arms contains a probe head within the pivot structure. The unused length of arms are stored in a compact manner, such as on a reel. The stiffness of the unfurled arms is obtained by increasing the section modulus of the arms as they are unfurled. Means are provided to securely hold the unfurled arms at the pivot so that arm motion is constrained in a direction perpendicular to rotation.

Figure 1:
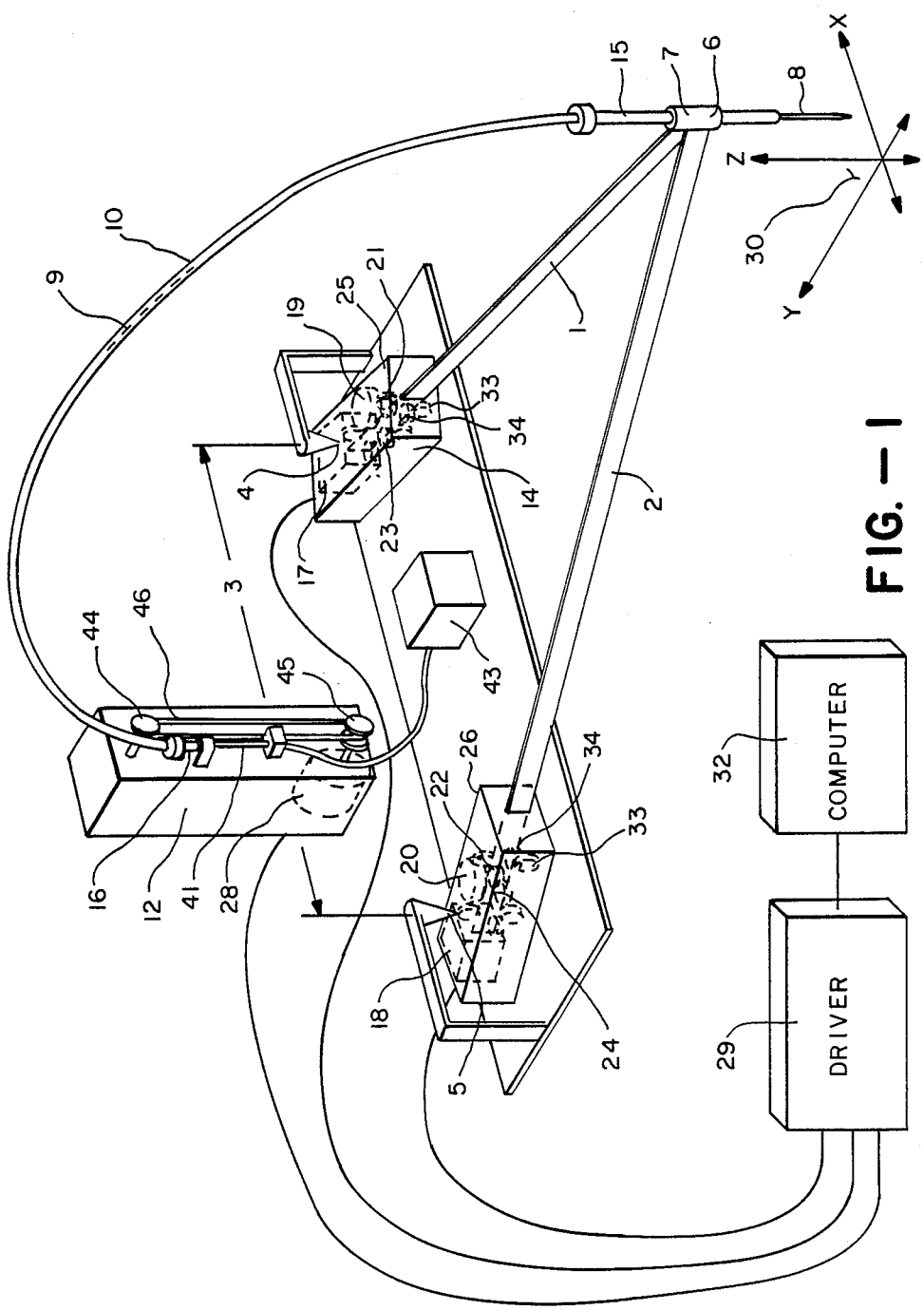
FIG. 1 depicts a diagram of an XYZ positioner according to the present invention.

Referring now to FIG. 1, a diagram of an improved XYZ positioner according to the present invention is depicted. The XYZ positioner has two variable length arms 1 and 2 and a "fixed length arm" 3. The three arms are connected with pivots 4 and 5 and hinge 6. In one embodiment, pivots 4, 5 are separated by a fixed length, which could be a suitable fixed arm 3. However, the present invention may be configured without a fixed arm between the pivots 4, 5 such as by providing a support frame for pivots 4, 5 or by placing pivots 4, 5 in a "fixed" position. The variable length arms 1 and 2 are connected to probe head 7, which provides an attachment for probe 8, probe actuation and flow tube 9 and Z-motion linear actuation guide tube 10.

Probe head 7 provides guide bearings for probe 8, which moves in a Z direction. Probe 8 is actuated in a Z axis direction by the flexible probe actuation and flow tube 9 sliding linearly inside linear actuation guide tube 10. This tube is linearly driven by Z drive motor 28 acting through pulleys 44 and 45 and belt 46 which is connected to Z drive rigid actuator tube 41, which is connected to the motor driven end of probe actuation and flow tube 9.

The end of rigid actuator tube 41 is guided within rigid actuation guide tube 16 which is fixed to Z-drive structure 12.

One end of the flexible linear actuation guide tube 10 is anchored to Z drive rigid actuator guide tube 16 and the other end is anchored to probe guide tube 15 of probe head 7. Linear actuation guide tube 10 provides support, a linear bearing surface, and accuracy for probe actuation and flow tube 9.

Fluid flow to probe 8 is generated by any fluid pressure means such as a pump or pressurized supply. Fluid is ported from fluid source and tube assembly 43 to the end of the Z-drive rigid actuator tube 41, through probe actuation and flow tube 9, through probe 8 to its target in target field 30.

Variable length arms 1 and 2 are desirably made of curved spring steel similar to a carpenter's tape. Arm motion perpendicular to the XY plane is constrained by arm guide bearings 33. Stepper drive motors 19 and 20 change the length of arms 1 and 2 to obtain a probe 8 XY position in target field 30. Stepper motors 19 and 20 drive arms 1 and 2 in and out via friction drive wheels 21 and 22 and pinch rollers 23 and 24.

As the length of the variable arms changes, arms 1 and 2 are reeled in and out of arm storage reels 17 and 18. These reels contain takeup spring motors similar to carpenter's tapes or other takeup means, such as an electric motor and slip clutch.

Turrets 13 and 14 are supported by, and pivot via, the stationary turret pivot points 4 and 5. Turrets 13 and 14 contain arm storage reels 17 and 18, stepper motors 19 and 20, friction drive wheels 21 and 22, pinch rollers 23 and 24, pressure rollers 34, guide bearings 33, turret frames 25 and 26, and other parts. Turret 13 may be a mirror image of turret 14.

A host computer 32 transmits desired XYZ coordinates to controller 29 via a suitable electrical cable. Controller 29 accepts XYZ coordinates and transforms these coordinates into motor control information to drive the two arm motors 19 and 20 and Z drive motor 28.

Figure 2:
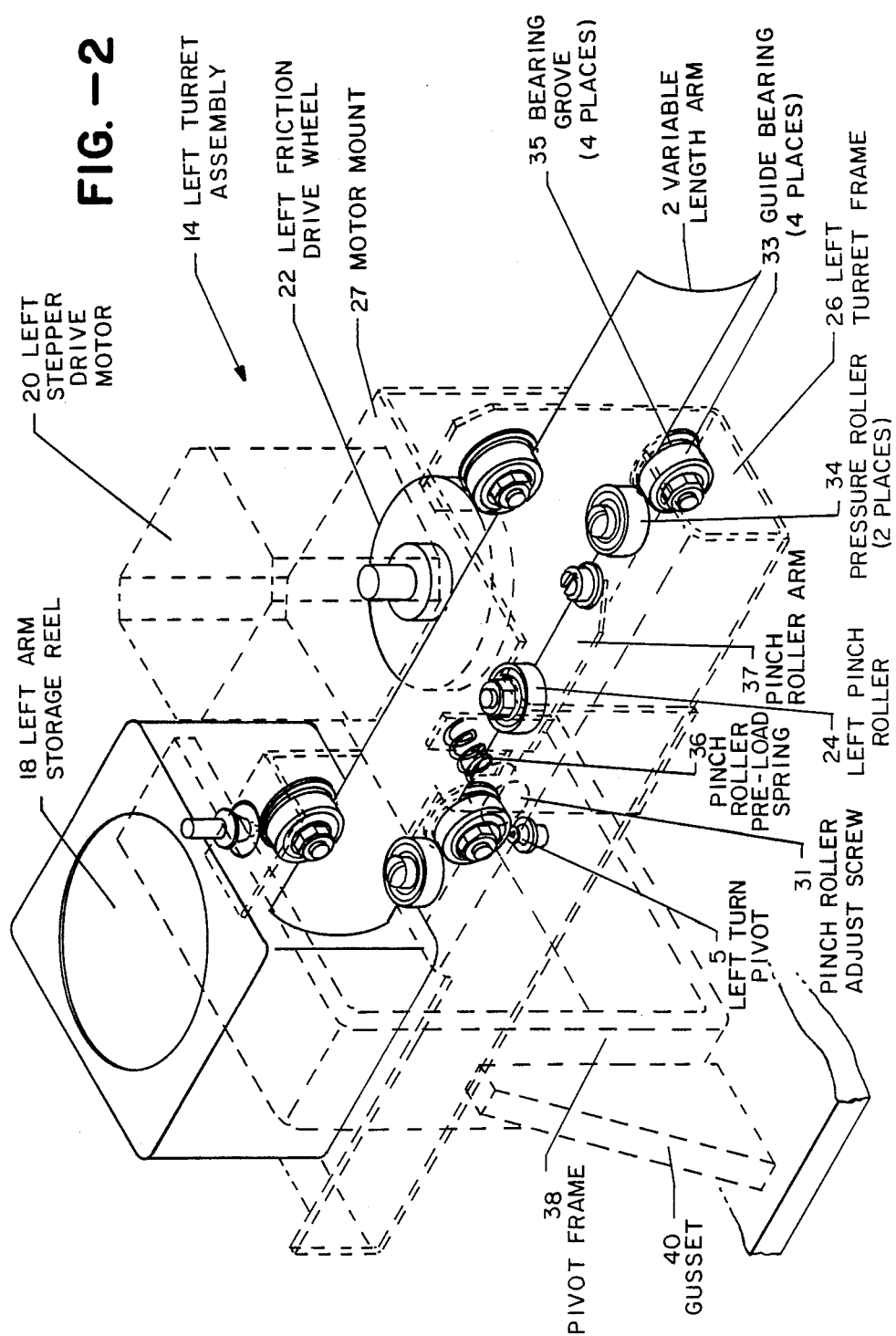
FIG. 2 depicts one preferred means to electromechanically implement a turret which form a portion of FIG. 1.

The present invention provides the capability of an increased section modulus to provide increased stiffness to the arms, which is obtained by making variable arms 1 and 2 out of a thin tape which curves similar to the way a carpenter tape curves as it unrolls. The curve is in the plane perpendicular to the long direction of the arm as shown in FIG. 2. During arm retraction, the arm cross-sections flattens as the arms are reeled around arm storage reels 17 and 18. Arm guides in the arm storage reel assemblies prevent arms 1 and 2 from unwinding when retracted. The means to change the arm length can be in the form of any type of linkage, such as rack and pinion, friction drive, hydraulic or any other form of actuation.

Figure 3:
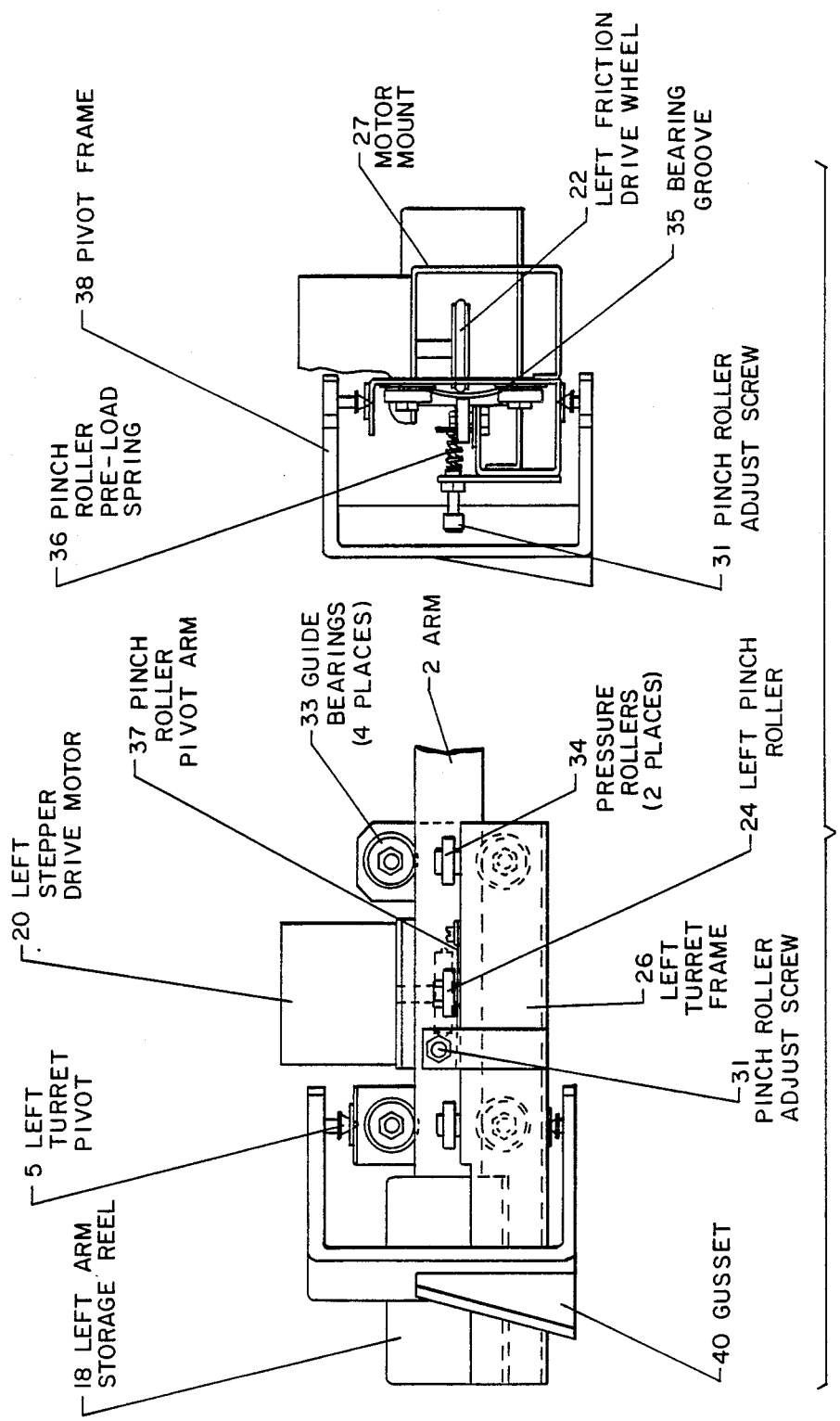
FIG. 3 depicts more detailed views of the turret of FIG. 2.

FIG. 2 illustrates one method of implementing the turret system of the present invention. Turret 14 is illustrated in FIG. 2 and in more detail in FIG. 3. Pivot frame 38 is mounted on base plate 39, which implements fixed length arm 3, and is supported by gusset 40.

Arm motion perpendicular to the XY plane is constrained by the guide bearing system. Variable length arm 2 is prevented from moving perpendicular to the XY plane by flanged arm guide bearings 33 and pressure rollers 34, which keep arm 2 in contact with arm guide bearings 33. The edges of arm 2 ride in bearing grooves 35.

Stepper drive motor 20, commanded by computer 32 and controller 29, drives arm 2 in and out via friction drive wheel 22. Pinch roller 24 is forced against arm 2 by pinch roller preload spring 36 and pinch roller pivot arm 37 to maintain adequate arm 2 drive traction for friction drive wheel 22. Preload pressure is adjusted via pinch roller pressure adjust screw 31.

Figure 4:
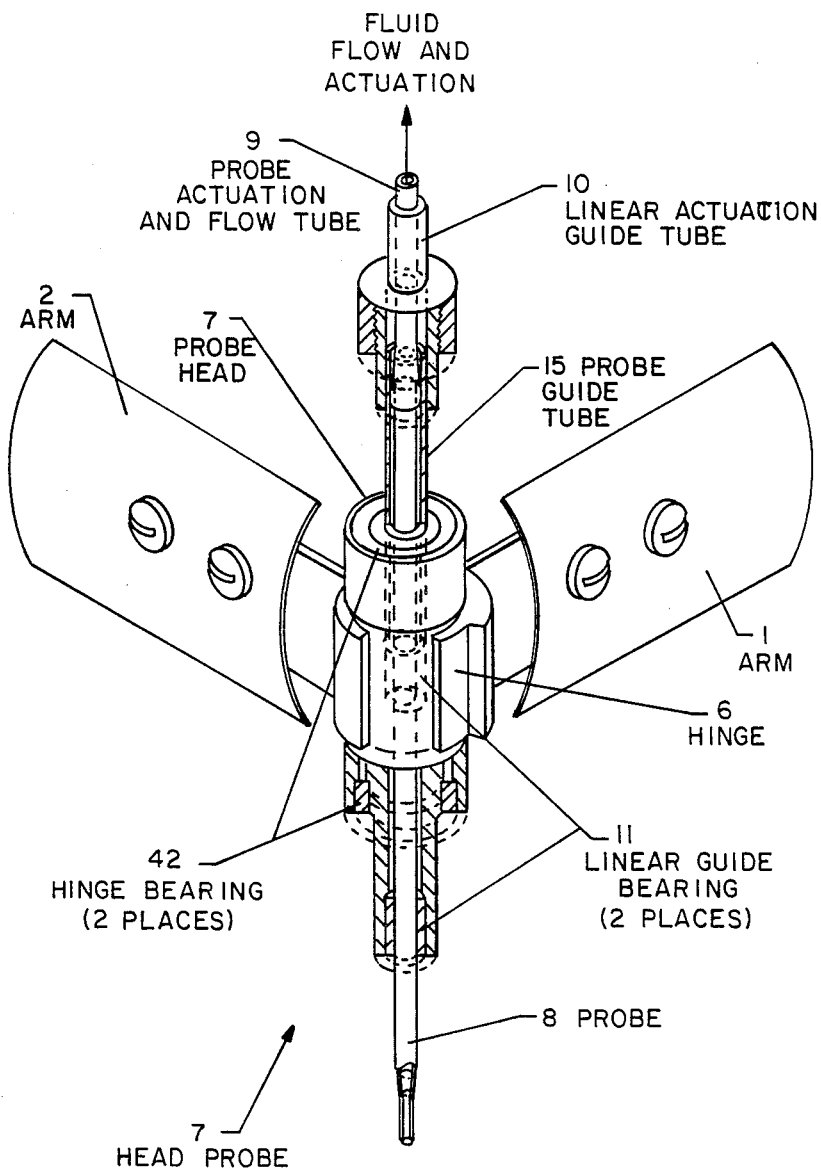
FIG. 4, depicts one means of implementing a probe head assembly which forms a portion of FIG. 1.

FIG. 4 illustrates one form of detailed mechanization of probe head 7. One end of linear actuation guide tube 10 is affixed to the end of rigid probe guide tube 15, which is affixed to the inner part of hinge 6, and which acts as a linear protective guide for probe 8. The linear probe actuation and flow tube 9 is connected to one end of probe 8.

Probe 8 is guided in probe head 7 by two linear probe guide bearings 11 and protective rigid probe guide tube 15. Probe head 7 also contains hinge 6 with two hinge bearings 42 to allow relative angular movement of arms 1 and 2 with respect to each other, as arms 1 and 2 extend and retract. Linear probe guide bearings 11 are mounted into the inner part of hinge 6, which is connected to arm 2, and allows both rotary and linear movement of probe 8. The outer part of hinge 6 is connected to arm 1 and can pivot in a limited arc around the inner part of hinge 6 via hinge bearings 42.

Probe head 7 can include any type of suitable hinge mechanism. The input of probe actuation and flow tube 9 can be connected to any source of liquid, gas, vacuum, light or pressure, which illustrates the many and wide range of applications for the present invention. The output of the tube is connected at the probe head and can deliver either liquid, gas, vacuum, light or pressure.

The Z drive prime mover may or may not be located on the arms. The Z drive prime mover can be connected to the probe head via a linear actuator similar to a bicycle brake cable. The Z drive actuation means can be via a linear cable or other means separate from the flow tube. The XYZ positioner desirably includes a flexible hollow tube as the Z drive member.

The present invention can incorporate a third variable length arm which could be located either in the same plane or at any angle to the plane of variable length arms 1 and 2 of FIG. 1.

The drive systems can be either open loop or closed loop control. The stepper motors can be changed to a mix or match of either servo motors and encoders, synchronous motors, hydraulic motors, pneumatic motors, or other rotary or linear motive device. The arm drive can be by friction rollers, sprockets, or other means.

The present invention can incorporate a tool holder and a detachable modular tool on the probe head, which would allow it to do a number of different functions such as drilling, welding, soldering, rotating, moving or other functions, simply by changing the tool, either manually or automatically. The particular tool utilized, whether it is removable or fixed at the probe head, can be powered electrically, hydraulically or pneumatically. One or more rotary actuations can also be incorporated in the head to give XYZ and rotary motions.

The motors can be replaced by encoders to provide a device which is a digitizer rather than a positioner.

Figure 5:
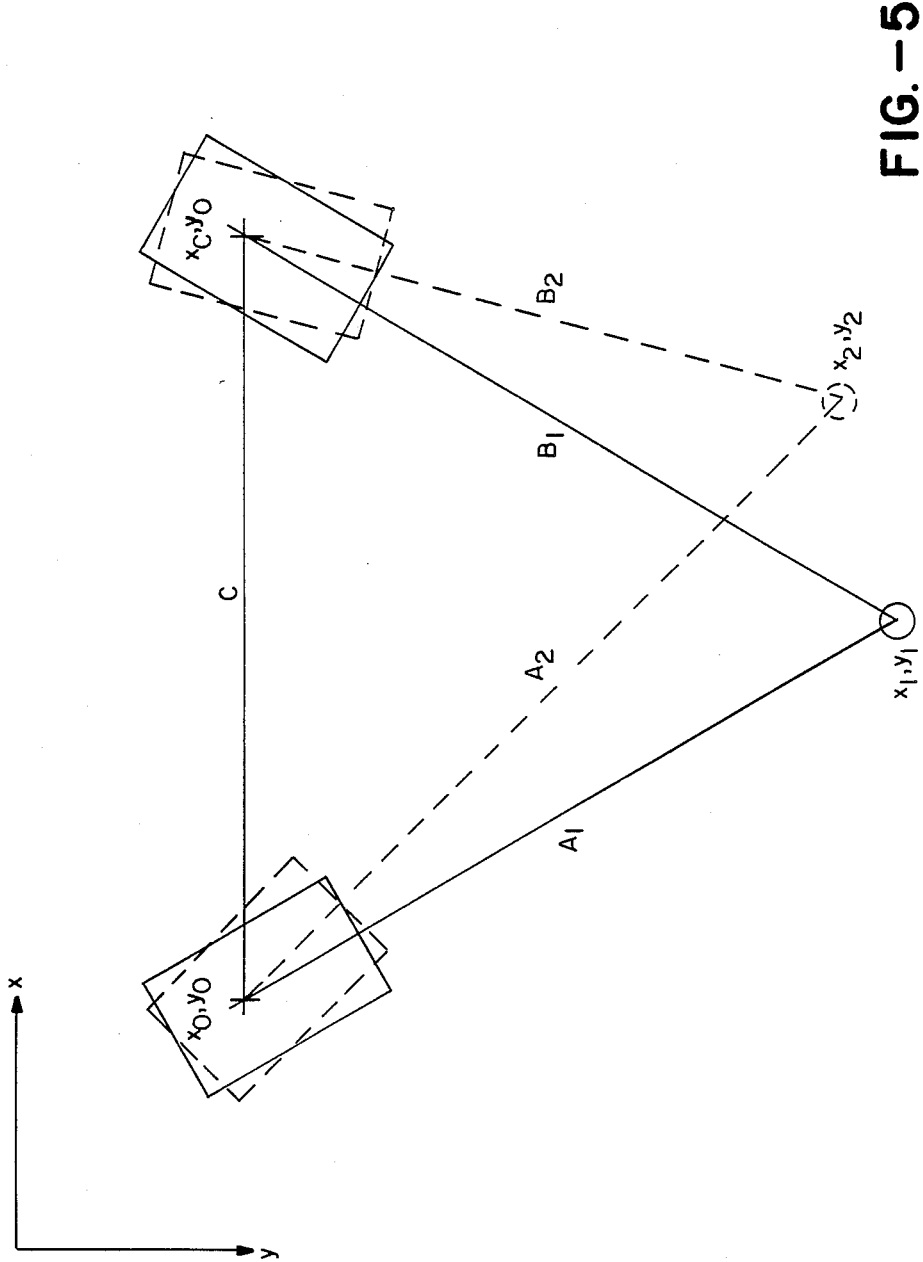
FIG. 5, depicts a diagram for explaining the changing of the variable length arms of FIG. 1.

Referring now to FIG. 5, a diagram is depicted therein for illustrating in an XY orientation how the variable length arms A, B can be changed to provide for movement to any desired position $X_n$, $Y_n$.

In FIG. 5, by changing the length of arm A and arm B, the location of the point where they join may be changed to any given position $X_n$, $Y_n$. The necessary A and B arm lengths, with a fixed length C therebetween, where $X_n$, $Y_n$ is the desired position are $$A_n = \sqrt{(Y_n - Y_o)^2 + (X_n - X_o)^2}$$

$$B_n = \sqrt{(Y_n - Y_o)^2 + (X_c - X_n)^2}$$

Hence, if the fixed length distance C equals 4.5 inches, and the desired position X1, Y1 is X1=2.25 inches and Y1=4 inches, then the required length of arms A and B will be $A_1=4.589$ and B1 equal 4.589.

For a situation where the fixed arm length C is still 4.5 inches, and the desired position is X2=3.7 inches, and Y2 =3.7 inches, then the variable arm lengths will be changed for A2=5.233 and B2=3.785 inches.

It can be seen, then, that by providing the proper control instructions for the desired position in an XY or XYZ orientation, the necessary change to the variable length arms can be easily calculated.

Figure 6:
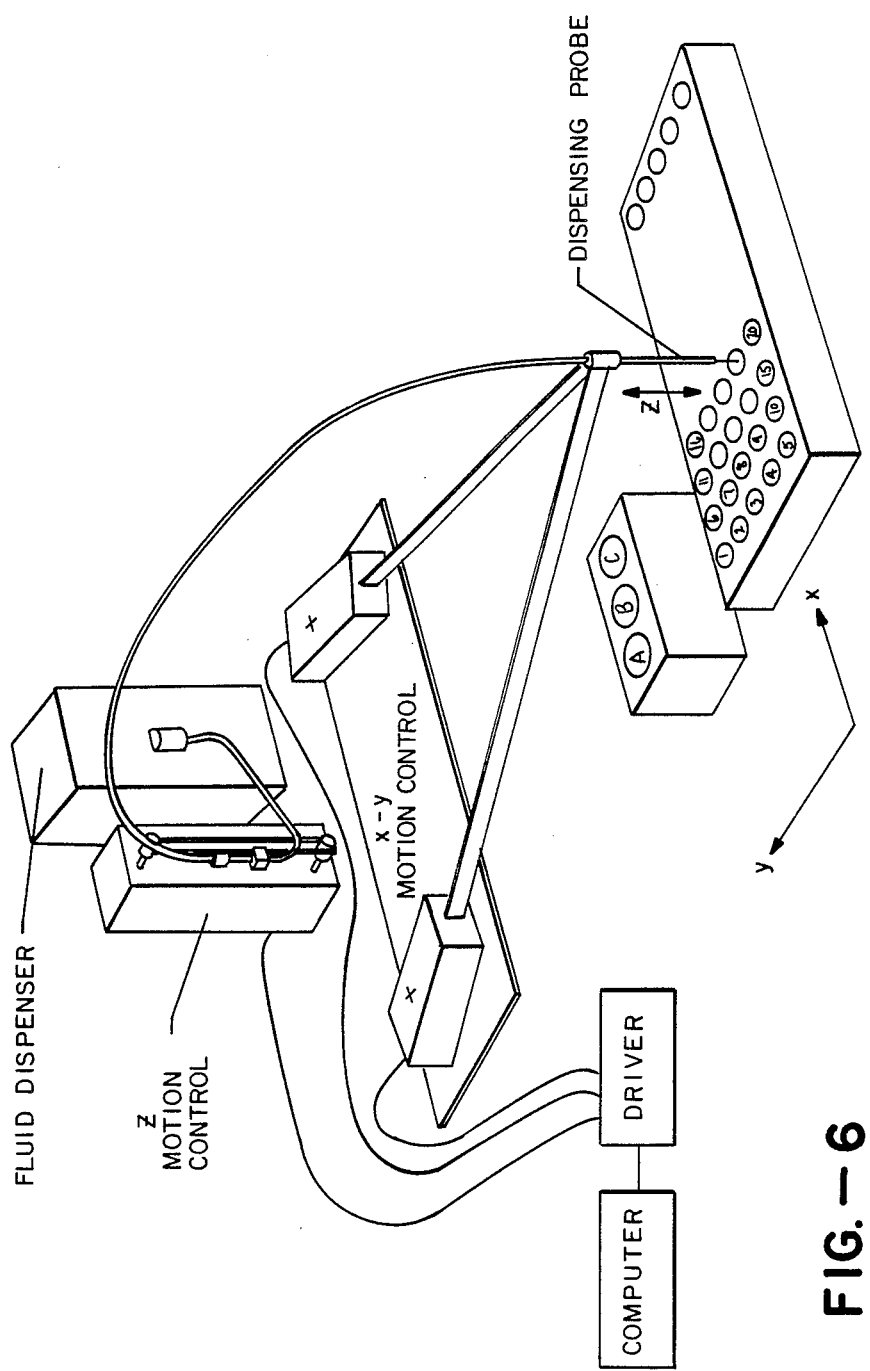
FIG. 6 depicts a diagram of a fluid dispenser system for describing a cycle of operation of the present invention.

Referring now to FIG. 6, a fluid dispensing system incorporating the aspects of the present invention is depicted. An illustrative cycle of operation for a fluid dispensing system incorporating the aspects of the present invention will now be described in detail in conjunction with FIG. 6.

By changing the length of the two variable length arms, the XY position of the probe may be changed, as desired. The Z motion controller can raise or lower the probe out of, or into, the container at any give X-Y position. The fluid dispenser can draw or dispense fluid through the probe.

A typical sequence would be as follows (the system element used for the function is indicated in parentheses).

1. Move the probe to position A (X-Y)
2. Lower the probe into the fluid (Z)
3. Draw fluid from A into the probe (Fluid Dispenser)
4. Raise probe out of A (Z)
5. Move probe to Position 1 (X-Y)
6. Lower probe to just above Position 1 (Z)
7. Dispense fluid into Position 1 (Fluid Dispenser)
8. Raise probe (Z)
9. Move probe to Position B (XY)
10. Lower the probe into the fluid (Z)
11. Draw fluid from B into the probe (Fluid Dispenser)
12. Raise the probe (Z)
13. Move to Position 2 (X-Y)
14. Lower the probe to just about Position 2 (Z)
15. Dispense fluid into Position 2 (Fluid Dispenser)
16. Raise the probe (Z)

By using the X-Y, Z and Fluid Dispenser elements, any combination of moves may be put together to create sequences such as the above.

According to a further aspect of the present invention, an example of a "pick and place" application will now be described, in conjunction with FIG. 7.

Figure 7:
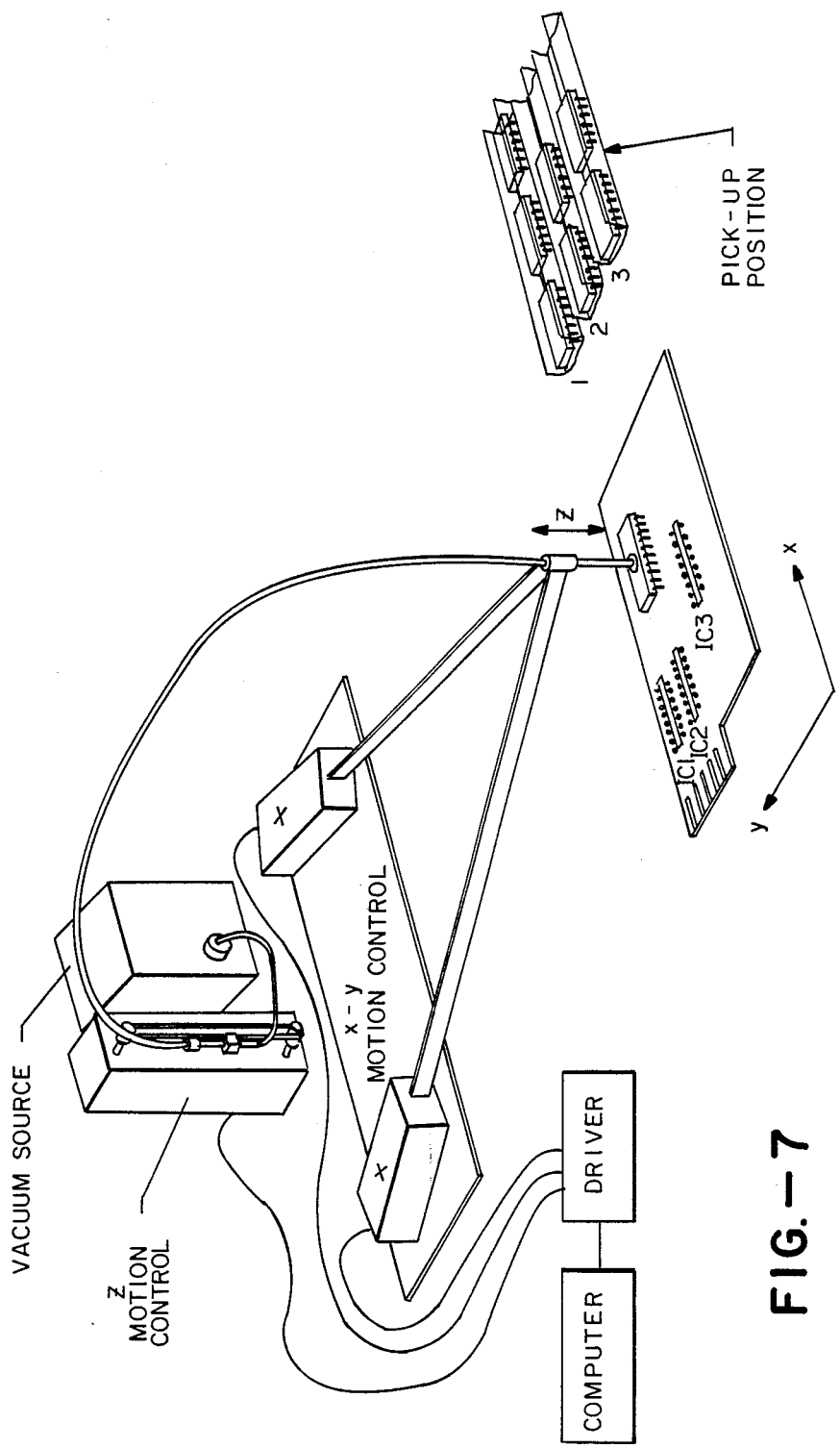
FIG. 7 depicts a diagram of a pick and place application utilized in conjunction with describing another cycle of operation of the present invention.

FIG. 7 depicts an aspect where integrated circuits (IC) are loaded onto a printed circuit board. By using an XYZ positioner according to the present invention, and using a pickup device such as a vacuum pickup head, IC components can easily be loaded into necessary desired locations on a printed circuit board.

A typical sequence for an illustrative cycle of operation for the present invention in a pick and place application would be as follows (again, where a system element used for function is indicated in parentheses) in conjunction with FIG. 7.

1. Move the head to Pickup Position 1 (X-Y)
2. Lower the head to touch the IC (Z)
3. Turn on Vacuum to pick up IC (Vacuum Source)
4. Raise head (Z)
5. Move to Position IC1 (X-Y)
6. Lower head to place IC on PC Board (Z)
7. Turn off Vacuum to release IC (Vacuum Source)
8. Raise head (Z)
9. Move to pick up Position 2 (X-Y)
10. Lower head to touch IC (Z)
11. Turn on Vacuum to pick up IC (Vacuum Source)
12. Raise head (Z)
13. Move to Position IC2 (X-Y)
14. Lower head to place IC on PC Board (Z)
15. Turn off Vacuum to release IC (Vacuum Source)
16. Raise head (Z)

It should be clear that the aspects of the present invention have many applications, and are not limited to, for example, a fluid dispensing system or a pick and place application. The present invention can be utilized in virtually any type of application which requires an XY or XYZ type of orientation. Therefore, the aspects of the present invention should be construed only in conjunction with the accompanying claims.

What is claimed is:

1. An XY positioner comprising
first and second self-suspending sufficiently flexible variable length arms where one end of said first and second variable length arms are connected to first and second turrets at first and second turret positions, respectively,
pivot means connecting the other end of said first and second arms in a pivoting relationship with one another wherein said first and second arms are connected together to form a changeable pivot position, and
control means for changing the length of said first and second arms to obtain a desired XY position, said control means including means for rolling and unrolling said first and second arms wherein said first and second arms either roll or unroll such that said variable lengths change between the respective first and second turret positions and said desired XY position.

2. An XY positioner comprising
first and second self-suspending sufficiently flexible variable length arms, where one end of said first and second variable length arms are connected to first and second turrets at first and second turret positions, respectively,
a third arm,
pivot means connecting said first, second and third arms in a pivoting relationship with one another wherein the other end of said first and second arms are connected together to form a changeable pivot position,
control means for changing the length of said first and second arms to obtain a desired XY position, said control means including means for rolling and unrolling said first and second arms wherein said first and second arms either roll or unroll such that said variable lengths change between the respective first and second turret positions and said desired pivot position.

3. An XYZ positioner comprising
first and second self-suspending sufficiently flexible variable length arms where one end of said first and second variable length arms are connected to first and second turrets at first and second turret positions, respectively,
pivot means connecting the other ends of said first and second arms in a pivoting relationship with one another wherein said first and second arms are connected together to form a changeable pivot position, wherein said first and second variable length arms are normally in a rolled or furled position, and wherein said variable length arms each have a sufficient section modulus to provide proper stiffness as each of said arms are either rolled or unrolled to obtain a stable XYZ position, and control means for changing the length of said first and second arms to obtain a desired XY position, said control means including means for rolling and unrolling said first and second arms wherein said first and second arms either roll or unroll such that said variable lengths change between the respective first and second turret positions and said desired pivot positions.

4. An XYZ positioner as in claim 3 wherein said positioner includes a linear type flexible actuator connected to said pivot position to provide for Z axis motion.

5. In a fluid aspirating system, an XY positioner comprising first and second self-suspending sufficiently flexible variable length arms where one end of said first and second variable length arms are connected to first and second turrets at first and second turret positions, respectively.

pivot means connecting the other ends of said first and second arms in a pivoting relationship with one another wherein said first and second arms are connected together to form a changeable pivot position, wherein said first and second variable length arms are normally in a rolled or furled position, and wherein said variable length arms each have a sufficient section modulus to provide proper stiffness as each of said arms are rolled or unrolled to obtain a stable XY position, and control means for changing the length of said first and second arms to obtain a desired XY position, said control means including means for rolling and unrolling said first and second arms wherein said first and second arms either roll or unroll such that said variable lengths change between the respective first and second turret positions and said desired pivot position.

6. An XYZ positioner comprising first and second self-suspending sufficiently flexible variable length arms are where one end of said first and second variable length arms are connected to first and second turrets at first and second turret positions, respectively, pivot means connecting the other ends of said first and second arms in a pivoting relationship with one another wherein said first and second arms are connected together to form a changeable pivot position, control means for changing the length of said first and second arms to obtain a desired XY position, said control means including means for rolling and unrolling said first and second arms wherein said first and second arms either roll or unroll such that said variable lengths change between the respective first and second turret positions and said desired pivot position, said control means further including means for controlling the positioning of said pivot means in a desired Z position.

7. An XYZ positioner as in claim 6 wherein said positioner includes a linear type flexible actuator connected to said pivot position.

8. An XYZ positioner as in claim 7 wherein said flexible actuator includes means for carrying fluid for dispensing as desired in said Z position.

9. An XYZ positioner as in claim 8 wherein said flexible actuator is self-lubricating.

10. In a fluid aspirating system, an XYZ positioner comprising first and second self-suspending sufficiently flexible variable length arms where one end of said first and second variable length arms are connected to said first and second turrets at first and second turret positions, respectively, a third fixed length arm, pivot means connecting said first, second and third arms in a pivoting relationship with one another wherein the other ends of said first and second arms are connected together to form a changeable probe position, control means for changing the length of said first and second arms to obtain a desired XY position, said control means including means for rolling and unrolling said first and second arms wherein said first and second arms either roll or unroll such that said variable lengths change between the respective first and second turret positions and said desired pivot position further including means for controlling the position of said probe position in a desired Z position, flexible cable means connected to said probe position and to said fluid aspirating system, said positioner including means for controlling the aspirating of fluid through said flexible cable means to one or more desired XY positions wherein said fluid is aspirated, as desired, in a specific XYZ position.

11. An XYZ positioner comprising first and second self-suspending sufficiently flexible variable length arms where one end of said first and second variable length arms are connected to first and second turrets at first and second turret positions, respectively, pivot means connecting the other ends of said first and second arms in a pivoting relationship with one another wherein said first and second arms are connected together to form a changeable pivot position, control means for changing the length of said first and second arms to obtain a desired XY position, said control means including means for rolling and unrolling said first and second arms wherein said first and second arms either roll or unroll such that said variable lengths change between the respective first and second turret positions and said desired pivot position, said control means further including position actuator means for controlling the positioning of said pivot means in a desired Z position.

12. An XYZ positioner comprising first and second self-suspending sufficiently flexible variable length arms where one end of said first and second variable length arms are at first and second turret positions, respectively, pivot means connecting the other ends of said first and second arms in a pivoting relationship with one another wherein said first and second arms are connected together to form a changeable position, control means for changing the length and position of said first and second arms to obtain a desired XYZ position, said control means including means for rolling and unrolling said first and second arms wherein said first and second arms either roll or unroll such that said variable lengths change between the respective first and second turret positions and said desired pivot position.

13. An XYZ positioner comprising an X positioner and a Y positioner to provide an XY position and at least one Z axis positioner including a Z motor wherein the Z positioner is a linear type flexible actuator connected to said X positioner and said Y positioner at said XY position and wherein said Z motor is stationary and remotely located from said Z positioner, and wherein said Z positioner includes a flexible hollow tube which slides internally to said flexible actuator in an up and down fashion to that a probe can be raised or lowered, respectively, at a desired Z position.

14. An XYZ positioner as in claim 13 wherein said flexible actuator includes means for carrying fluid for dispensing or aspirating in a desired position.

15. An XYZ positioner as in claim 14 wherein said flexible actuator is self-lubricating.

16. In a fluid aspirating system, a positioner comprising
  a probe,
  an XY positioner for positioning said probe in an XY position,
  control means for changing the position of said probe in a desired Z direction,
  a flexible actuator connected to said probe and to said fluid aspirating system, said positioner including means for controlling the aspirating of fluid and controlling the Z position through said flexible actuator to one or more desired XY positions wherein said fluid is aspirated, as desired, at a specific position.

17. A fluid aspirating system comprising
  a one-axis positioner wherein fluid is delivered and one-axis motion is obtained using a flexible linear actuator cable having a center portion, wherein the center portion of said cable which provides the motion also conducts the fluid, wherein said one-axis positioner includes a flexible hollow tube which slides internally to said flexible actuator in an up and down fashion so that said probe can be raised or lowered, respectively, at a desired position.

18. A fluid aspirating system as in claim 17 including actuator means, control means and fluid fittings at the input end of said flexible cable.

19. In a fluid dispensing system, an XY positioner comprising
  first and second self-suspending sufficiently flexible variable length arms where one end of said first and second variable length arms are connected to first and second turrets at first and second turret positions, respectively,
  pivot means connecting the other ends of said first and second arms in a pivoting relationship with one another wherein said first and second arms are connected together to form a changeable pivot position, wherein said first and second variable length arms are normally in a rolled or furled position, and wherein said variable length arms each have a sufficient section modulus to provide proper stiffness as each of said arms are rolled or unrolled to obtain a stable XY position, and
  control means for changing the length of said first and second arms to obtain a desired XY position, said control means including means for rolling and unrolling said first and second arms wherein first and second arms either roll or unroll such that said variable lengths change between the respective first and second turret positions and said desired pivot position.

20. In a fluid dispensing system, an XYZ positioner comprising
  first and second self-suspending sufficiently flexible variable length arms where one end of said first and second variable length arms are connected to first and second turrets at first and second turret positions, respectively,
  a third fixed length arm,
  pivot means connecting said first, second and third arms in a pivoting relationship with one another wherein the other ends of said first and second arms are connected together to form a changeable probe position,
  control means for changing the length of said first and second arms to obtain a desired XY position, said control means including means for rolling and unrolling said first and second arms wherein said first and second arms either roll or unroll such that said variable lengths change between the respective first and second turret positions and said desired pivot position, further including means for controlling the position of said probe position in a desired Z position,
  flexible cable means connected to said probe position and to said fluid dispensing system, said positioner including means for controlling the dispensing of fluid through said flexible cable means to one or more desired XY positions wherein said fluid is dispensed as desired in a specific XYZ position.

21. In a fluid dispensing system, a positioner comprising
  a probe,
  an XY positioner for positioning said probe in an XY position,
  control means for changing the position of said probe in a desired Z direction,
  a flexible actuator connected to said probe and to said fluid dispensing system, said positioner including means for controlling the Z position through said flexible cable means to one or more desired XY positions wherein said fluid is dispensed as desired in a specific position.

22. A fluid dispensing system comprising
  a one-axis positioner wherein fluid is delivered and one-axis motion is obtained using a flexible linear actuator cable having a center portion, wherein the center portion of said cable which provides the motion also conducts the fluid, wherein said one-axis positioner includes a flexible hollow tube which slides internally to said flexible actuator in an up and down fashion so that a probe can be raised or lowered, respectively, at a desired position.

23. A fluid dispensing system as in claim 22 including actuator means, control means and fluid fittings at the input end of said flexible cable.

* * * * *